United States Patent [19]

Garby et al.

[11] Patent Number: 5,242,067

[45] Date of Patent: Sep. 7, 1993

[54] ADAPTOR FOR INDICATOR DEVICE

[75] Inventors: Gage Garby; Allan Barker, both of Boulder, Colo.

[73] Assignee: Senetics, Inc., Boulder, Colo.

[21] Appl. No.: 786,115

[22] Filed: Nov. 1, 1991

Related U.S. Application Data

[63] Continuation-in-part of Ser. No. 718,354, Jun. 21, 1991, which is a continuation-in-part of Ser. No. 641,759, Jan. 17, 1991, which is a continuation-in-part of Ser. No. 306,485, Feb. 3, 1989, Pat. No. 5,009,338.

[51] Int. Cl.$^5$ .................... B65D 51/24; B65D 51/18
[52] U.S. Cl. .................... 215/230; 215/216; 215/226; 215/303
[58] Field of Search .............. 215/230, 203, 204, 216, 215/220, 226, 232, 274, 301, 303

[56] References Cited

U.S. PATENT DOCUMENTS

| | | |
|---|---|---|
| 3,233,769 | 2/1966 | Jessop ................................ 215/216 |
| 3,604,582 | 9/1971 | Boudin ............................ 215/216 X |
| 3,642,161 | 2/1972 | Stroud ............................. 215/216 X |
| 3,977,554 | 8/1976 | Costa ................................... 215/220 |
| 4,011,829 | 3/1977 | Wachsmann et al. .......... 215/216 X |
| 4,393,977 | 7/1983 | Willingham ........................ 215/211 |
| 4,402,416 | 9/1983 | Mumford et al. ................... 215/220 |
| 4,410,098 | 10/1983 | Dubs et al. .......................... 215/220 |
| 4,500,005 | 2/1985 | Forrester ............................ 215/203 |
| 4,749,093 | 6/1988 | Trick .................................. 215/220 |
| 5,009,338 | 4/1991 | Barker ................................ 215/230 |

Primary Examiner—Allan N. Shoap
Assistant Examiner—Vanessa Caretto
Attorney, Agent, or Firm—Beaton & Swanson

[57] ABSTRACT

An adaptor for use with an indicator device, comprising a ring-shaped element having an inner circumference for attaching to the indicator device and an outer circumference for grasping by the user in order to manipulate the indicator device. The inner circumference has an upper radial lip and lower radial lip that maintain the indicator device therebetween, and the outer circumference may have grasping-enhancing elements such as a set of circumferential knobs.

7 Claims, 2 Drawing Sheets

ADAPTOR FOR INDICATOR DEVICE

This application is a continuation-in-part of application Ser. No. 07/718,354 filed Jun 21, 1991 which is a continuation-in-part of application Ser. No. 07/641,759 filed Jan. 17, 1991, which is a continuation-in-part of application Ser. No. 07/306,485 filed Feb. 3, 1989 now U.S. Pat. No. 5,009,338.

BACKGROUND THE OF INVENTION

The present invention relates to closure members for containers, bottles and the like and, more particularly, to closure members having indicator means to indicate the number of times the container has been opened. The invention can also be used for any other application in which the number of times a given activity is performed must be indicated.

In the medical field, medical drugs have a predetermined therapeutic range in which the effects of taking the drug are beneficial. Under-utilization of a drug may endanger the user with the drug's side effects without reaching levels necessary for a therapeutic action. On the other hand, over-utilization may cause side effects or toxicity to a much greater extent than any possible benefit. Thus it is critically important that a patient follow prescribed directions on medications, yet frequently patients forget whether they have taken medication and either omit doses or repeat them.

A considerable number of pill-timing schemes have been used to solve the problem of reminding a patient to take a dose of medicine or reminding him he has already taken the dose. The most used ones involve some scheme of compartmentalization of the necessary medication, such that the pills are placed in compartments that are labeled by day, dose number of time of day, or that are serially numbered. These devices are reasonably satisfactory if a responsible person is available and has the time and patience to fill the compartments properly.

In dispensing pills of a single type, a number of window-containing bottle caps have been invented. Through the window a movable element marked with an index is visible. In only a few devices does the indicating element index in position relative to the window each time the cap is loosened, removed, replaced, and retightened. Thus, by looking at the index mark displayed through the window, a user can see where in repetitive sequence of dose he or she is.

One of the most serious disadvantages of prior art devices of the window indexing type is that there is no warning to the user in case the user does not turn the device far enough during the opening or closing to properly advance the window. Unless the user is alert to the index value before opening and then after closing such devices, the user will be unaware that the window failed to advance to a new index. Most users, especially the elderly who may not understand how the device operates, will not be this alert to the functioning of the device. In addition, most prior art devices fail to provide positive locking in both directions of movement; thus, the index may be moved appropriately when the device is opened or closed, but additional movement is not prevented when the device is moved in the opposite direction. This allows the index to drift, often causing failure or an incorrect reading, particularly after the device has been used over a period of time.

The device of U.S. Pat. No. 4,011,829 issued Mar. 15, 1977 to Wachsmann, et al., attempts to provide positive locking in both directions, but because of the direction of the tooth designed to prevent movement of the index upon closure, the device may not work reliably, particularly after wearing with use. Also, the device of Wachsmann does not provide space for the ratchet teeth to slide past the engagement teeth when the device is moving in a direction wherein such teeth should disengage, which may cause unreliable operation over a period of time. Another drawback of this device is its inclusion of a complicated "child proofing" feature with the indexing feature, which makes the device quite complex. Other features of this device, such as the method of providing the lost motion drive and the requirement of a post in the middle of the elements to hold the device together, also increase its complexity.

The device of U.S. Pat. No. 3,151,599 issued Oct. 6, 1964 to Livingston provides positive locking in both directions, but it does so by means of very closely spaced projections that would be difficult to manufacture economically. Furthermore, this device does not provide space for the projections to move while sliding past each other when not engaged.

The device of U.S. Pat. No. 4,666,051 issued May 19, 1987 to Trick has an indicator wheel with a serrated rim projecting above and below the plane of the wheel. The serrations engage mating serrations in upper and lower elements in order to drive the indicator mechanism. The serrations are rigid and, therefore, tend to wear excessively as they slide past one another.

It is also apparent from a review of this art that there is a need for an improved indicator cap that can be used as a child-resistant closure. Preferably, such a cap would have a minimum of parts, would be easily manufactured and assembled using standard injection molding and assembly methods, and could be used with ordinary containers that are not necessarily specially designed for the cap.

It is also apparent from a review of this art that the prior art devices are generally designed for attachment to a container of a particular size. For example, the Wachsmann device is a cap with indicating features that is designed with threads that fit into a particular threaded container. Other devices may include a skirt portion on the outer shell of the device that fits over a standard cap of a container so that the standard cap nests inside the skirt. Yet other devices may be substantially disk-shaped so that they can be attached directly to the top of a standard cap. The cap is removed from the container by grasping the device and turning it along with the standard cap to which it is attached, thereby advancing the indicator mechanism. In the case of these last two types of devices, the devices cannot be used effectively with standard caps that are too large. In the device with the skirt, a large standard cap will not rest into the skirt. In the disk-shaped device that is attached to the top of a standard cap, the device will be too small in relation to the cap to be gripped effectively and, instead, the user will inadvertently grip the standard cap itself so that the indicator mechanism is not advanced.

SUMMARY OF THE INVENTION

It is an object of the present invention to provide an indicator device to indicate the number of times a given event has occurred. Such an invention may have applicability in the control of chemical containers, the development of photographic film and many other areas.

In particular, it is an object of the present invention to provide a device to enlarge the outer circumference of a disk-shaped indicator mechanism, so that the outer circumference is easier to grasp to advance the indicator mechanism.

More particularly, it is an object of the present invention to provide an indicator cap for a medication dispensing bottle or the like that provides an indication each time the bottle is opened and then reclosed.

It is another object of this invention to provide a device that has positive control of the index member during both the opening and the closing motions and to require the advancement of the index member by one and only one new index during each complete opening and closing cycle.

Yet another object of the invention is to provide an audible sound to confirm that the device has been rotated sufficiently to move the index to the next location and to also provide an audible sound when the device has been rotated sufficiently to re-cock the device for the next open-close sequence.

Still another object is to provide space within the device for the locking mechanisms to slide past each other when not engaged to allow such mechanisms to work reliably over a long period of time.

Another object of the present invention is to combine functions usually requiring several components into single components to reduce the complexity of the device and provide ease of manufacturability and assembly using standard injection molding and assembly techniques.

Another object of the present invention is to provide an indicator assembly that can easily be fitted to an ordinary container without requiring any special modifications to the container itself.

Another object is to provide a device with indicator symbols that can be sensed by touch such as raised letters or braille.

Another object is to provide a device that can be easily grasped by elderly or impaired patients, as by including grasp-facilitating elements on the device.

Another object is to provide a device which is easily manufactured and assembled with a minimum of parts.

DETAILED DESCRIPTION OF THE INVENTION

Figure 1:
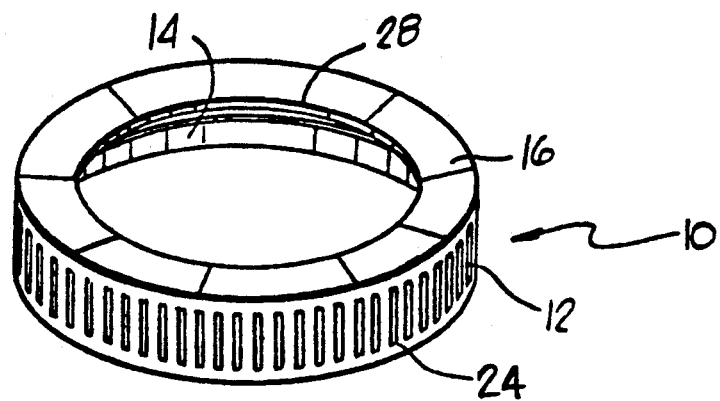
FIG. 1 shows a perspective view of the present invention.
Figure 2:
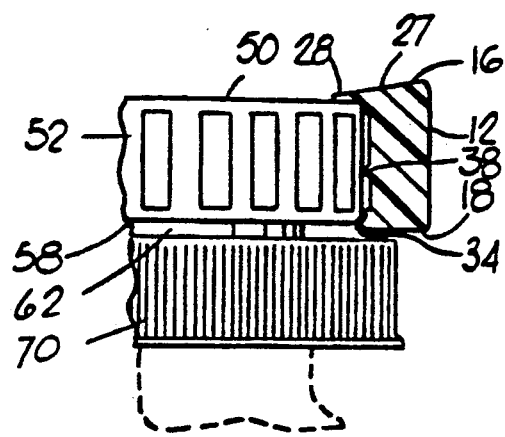
FIG. 2 shows a sectional view of the invention attached to a disk-shaped indicating device which is attached to a container cap.

A perspective view and a cross-sectional view of the invention are shown in FIGS. 1 and 2. The invention 10 is a ring-shaped element having an outer circumference 12, an inner circumference 14, a top 16 and a bottom 18. The outer circumference may have a set of knobs 24 to facilitate the grasping of the device. The inner circumference 14 may have an upper circumferential lip 28 extending radially inward from the top of the inner circumference which serves as a stop for the indicating mechanism in the manner described below. It may also have a lower circumferential lip 34 extending radially inward from the bottom of the inner circumference which serves as a lock for the indicating mechanism in the manner described below. There may be one or more intermediate circumferential lips 38 extending radially inward at levels intermediate between top and bottom to improve the attachment between the device and the indicator mechanism.

The top of the device may be chamfered in the manner shown in FIG. 2. The chamfer 27 is from the outer circumference 12 downward to the inner circumference 14 and includes the top of the upper circumferential lip 28 that extends radially inward. In this way, the device not only serves to enlarge the effective circumference of the indicator mechanism, but is also increases the effective height of the indicator mechanism. Both these features facilitate the grasping of the combined indicator mechanism and device.

The device may be made of any suitable durable material such as plastic, metal, wood or the like. Preferably, the device is resilient so that it can be deformably attached to the indicator mechanism, and is made of an injectionable thermoplastic.

Figure 3:
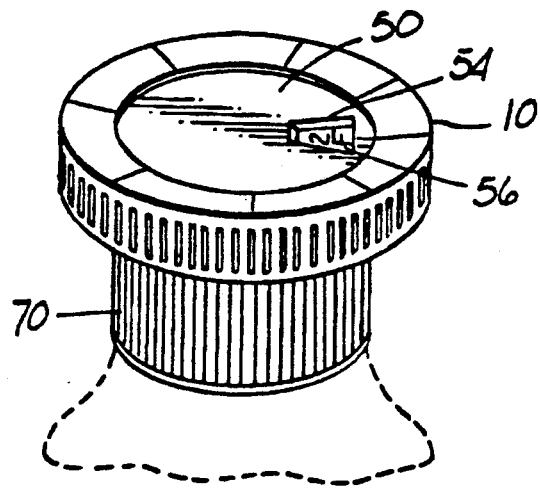
FIG. 3 shows a perspective view of the invention attached to a disk-shaped indicating device which is attached to a container cap.

The invention 10 is shown attached to an indicating device in FIGS. 2 and 3. The indicating device 50 includes an outer cover 52 having an indicating window 54 to view indicating symbols on an indicator wheel 56. A retainer wheel 58 is mounted on the outer cover 52 in a manner that allows limited rotation between the outer cover and the retainer wheel. The retainer wheel 58 holds the indicator wheel 56 in place. The retainer wheel 58 has a means for attaching the indicator device 50 to a cap 70 such as the double-sided adhesive pad 62 that is shown on the bottom of the retainer wheel. The outer cover 52, indicator wheel 56 and retainer wheel 58 include a means for advancing the indicator wheel past the indicator window 54 each time the device is cycled through an opening and closing of the container by rotating the device to remove and replace the cap. Such means may be the tooth and pawl arrangements taught in U.S. Pat. No. 5,009,338 by Barker, of which the present application is a continuation-in-part and the contents of which are hereby incorporated by reference, or the arrangements taught in other art such as U.S. Pat. No. 4,011,829 by Wachsmann et al. or U.S. Pat. No. 3,151,599 by Livingston or others. The present invention may be used in any indicator device in which it is desired to enlarge the effective circumference or height or both. The invention is especially useful in devices that have a rotational mechanism to advance the indicator symbols, and that are to be used on a container cap that is of a larger diameter than the device itself.

The invention 10 is pressed onto the indicating device 50 so that the indicating device 50 deforms the lower and intermediate circumferential lips 34 and 38, respectively, as it slides past them. The upper circumferential lip 28 extends radially inward sufficiently far to function as a stop against the top of the indicator mechanism 50. However, the upper circumferential lip 28 does not extend radially inward so far that it obscures the indicating window 54 or any printed matter on the indicating mechanism 50.

The distance from the top of the lower circumferential lip 34 to the bottom of the upper circumferential lip 28 is preferably approximately the same as the height of the indicating device 50. Therefore, as the upper circumferential lip 28 acts as a stop against the indicating device 50 as the invention 10 is pressed over the indicating device, the indicating device snaps past the lower circumferential lip 34 to lock the indicating device and the invention together. When locked together, the fit is sufficiently tight that there is no slippage of one past the other. The tightness of the fit may be enhanced by the inherent friction between the indicating device and the intermediate circumferential lip 38 and by other friction-enhancing elements such as ribs, serrations or surface roughness either the inner circumference 14 or on the indicating mechanism.

In operation, the combined invention 10 and indicator device 50 are attached to a container cap 70. The attachment of the indicator device and the invention to the cap may be any suitable means. In the embodiment shown in FIG. 2, the attachment is accomplished with a double-sided adhesive pad 62, one adhesive side of which is attached to the bottom of the retainer disk of the indicator device and the other adhesive side of which is attached to the top of the cap. It can be appreciated that the attachment of the invention to the indicator device in this manner serves to enlarge the effective diameter and circumference of the indicator device, so that the assembly extends past the periphery of the cap. This facilitates the grasping of the device when the user is removing or replacing the cap, so that the indicator mechanism properly advances. Without the invention, the indicator device would be too small to be grasped firmly and predictably, and the user would instead directly grasp the cap itself, so that the indicator mechanism would not properly advance.

It can be appreciated that the chamfer 27 between the outside circumference 12 downward to the inside circumference 14, serves to increase the effective height of the indicator device. This increase in effective height provides additional assistance in grasping the device.

It should also be appreciated that the contour of the outer circumference 12 need not be circular. Instead, it may be serrated or grooved or textured, or may have an aesthetic design such as a heart shape or another desired design.

Figure 4:
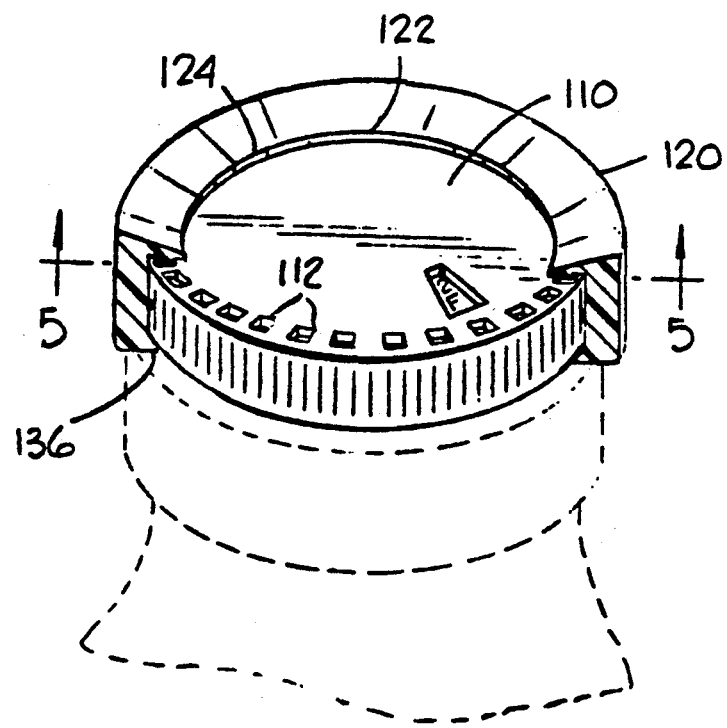
FIG. 4 is a partial perspective view of another embodiment of the invention.
Figure 5:
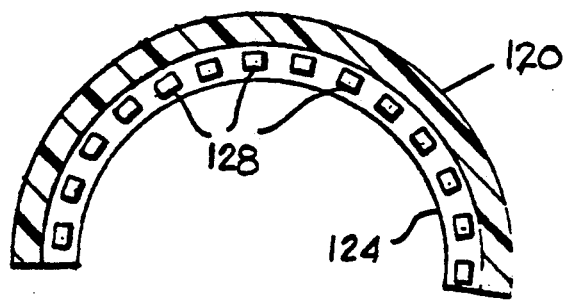
FIG. 5 is a sectional view, taken along line 5—5 of FIG. 4.

Another embodiment of the device which incorporates a child-resistant function is shown in FIGS. 4 and 5. A indicator device 110 is disk-shaped with a set of notches 112 spaced around its top surface. The indicator device functions in the manner previously described. The ring-shaped element 120 has a central hole 122 and an upper flange 124 extending radially into the hole.

A lower lip 136 around the bottom of the ring hole prevents the ring from being lifted off the indicator. The axial distance between the flange 124 and lower lip 136 is sufficiently great to allow play between the ring and the indicator to allow the tabs and notches described below to engage and disengage.

The lower surface of the flange 124 has a set of tabs 128 to mate with the notches on the upper surface of the indicator device. Preferably, the tabs and notches are shaped with appropriately sloping walls so that the tabs engage the notches upon rotation of the ring in a clockwise direction to close a container, but the tabs disengage the notches upon rotation of the ring in a counterclockwise direction to unclose a container. An axial force must be applied to urge the tabs into the grooves upon rotation in a counterclockwise direction. Since children will generally not recognize this, the device is thereby child-resistant.

What is claimed is:

1. An adaptor for attachment to an indicator device, the device being to indicate a removal or replacement of a closure from a container, wherein the closure is to be removed or replaced by application of a rotative force relative to the container about an axis of rotation, comprising a body extending perpendicular from the axis of rotation, the body having an outer surface for grasping, and means for removably securing the body to the indicator device, the body further including an inner surface to mate with the indicator device and an outer surface, the inner and outer surfaces being substantially cylindrical and coaxial, and the adaptor has an upper surface connecting the inner surface and outer surface, the upper surface being chamfered from a radially outer height downward to a radially inner height.

2. A device for attachment to a container closure, wherein the closure is to be removed or replaced by application of a rotative force relative to the container about an axis of rotation, comprising an indicator having a circular radially outer edge, wherein the indicator indicates that the closure has been replaced or removed from the container; means for attaching the device to the closure; and an adaptor removably attachable to the indicator that has an inner periphery that contacts said circular radially outer edge of the indicator and an outer periphery extending radially outward from the inner periphery, the indicator being substantially disk-shaped and the adaptor being substantially ring-shaped with a hole having an inner circumference that mates with the radially outer edge of the indicator, and the adaptor has an upper surface chamfered downward.

3. The device of claim 2, wherein the adaptor has an upper locking lip at the inner circumference extending radially inward past the adaptor inner circumference.

4. A device for attachment to a container closure, wherein the closure is to be removed or replaced by application of a rotative force relative to the container about an axis of rotation, comprising an indicator having a circular radially outer edge, wherein the indicator indicates that the closure has been replaced or removed from the container; means for attaching the device to the closure; and an adaptor removably attachable to the indicator that has an inner periphery that contacts said circular radially outer edge of the indicator and an outer periphery extending radially outward from the inner periphery; wherein the device includes means for resisting removal of the closure by a child including means that prevent a rotative force from being transferred from the device to the closure except upon application of a simultaneous axial force, including a plurality of axially extending elements on one of the adaptor and indicator device and a plurality of matching notches on the other of the adaptor and indicator device; and wherein said adaptor has a radially extending flange to limit axial movement of the adaptor relative to the indicator in a first axial direction, the flange having a bottom surface with one of the plurality of axially extending elements and plurality of mating notches and the indicator has an upper surface to mate with the flange bottom surface having the other of said one of the plurality of axial extending elements and mating notches.

5. The device of claim 4, wherein said adaptor has one of a stop and a stop-mate and the indicator has the other of a stop and a stop-mate to limit axial movement of the adaptor in a second direction opposite the first direction.

6. The device of claim 5, wherein the stop is a lip on the adaptor extending radially toward the indicator, and the stop-mate is the indicator.

7. The device of claim 6, wherein the lip and flange are sufficiently spaced such that the indicator and adaptor can move relative to one another to allow the axially extending elements and notches to engage and disengage.

* * * * *